United States Patent [19]

Wroblowsky

[11] Patent Number: 5,817,863

[45] Date of Patent: Oct. 6, 1998

[54] PROCESS AND NOVEL INTERMEDIATES FOR PREPARING TRIAZOLINONES

[75] Inventor: Heinz-Jürgen Wroblowsky, Langenfeld, Germany

[73] Assignee: Bayer Aktiengesellschaft, Leverkusen, Germany

[21] Appl. No.: 898,981

[22] Filed: Jul. 23, 1997

Related U.S. Application Data

[62] Division of Ser. No. 595,951, Feb. 6, 1996, Pat. No. 5,708,183.

[30] Foreign Application Priority Data

Feb. 13, 1995 [DE] Germany .................. 195 04 627.7

[51] Int. Cl.$^6$ ...................... C07C 281/02; C07C 281/04
[52] U.S. Cl. ................. 560/137; 560/30; 560/31; 560/115; 560/159
[58] Field of Search ............... 560/30, 31, 115, 560/137, 159

[56] References Cited

U.S. PATENT DOCUMENTS 4,282,169  8/1981  Rothgery et al. .............. 558/233

FOREIGN PATENT DOCUMENTS

| 0 577 394 A1 | 1/1994 | European Pat. Off. . |
| 2123205 | 9/1972 | France . |
| WO 94/19323 | 9/1994 | WIPO . |

OTHER PUBLICATIONS

J. Heterocyclic Chem. 22 pp. 1121–1126 (1985) (G.D. Madding et al).
Liebigs Ann. Chem. pp. 504–522 (1974) (H. Rochling et al).
Journal of Synthesis Organic Chem. pp. 350–352 (1991) (C. Astorga et al).
Uneyama et al (Tet.Let., 31 (19) pp. 2717–2718 (1990).
Ikizler et al (CA 116:25554m) (1992).
Cram & Hammond, Organic Chemistry, 2nd Edition, pp. 565–567 (1964).

Primary Examiner—Richard L. Raymond
Attorney, Agent, or Firm—Sprung Kramer Schaefer & Briscoe

[57] ABSTRACT

The present invention relates to a novel process for preparing triazolinones of the general formula (I)

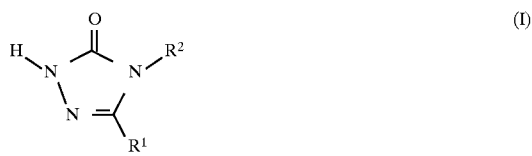

in which $R^1$ represents halogenoalkyl, and $R^2$ represents hydrogen, hydroxyl or amino, or represents alkyl, alkenyl, alkinyl, alkoxy, alkylamino, dialkylamino, cycloalkyl, cycloalkylalkyl, phenyl or phenylalkyl which are in each case optionally substituted, and also to novel intermediates for preparing these triazolinones and to processes for preparing the intermediates themselves.

2 Claims, No Drawings

PROCESS AND NOVEL INTERMEDIATES FOR PREPARING TRIAZOLINONES

This is a division of application Ser. No. 08/595,951, filed on Feb. 6, 1996, now U.S. Pat. No. 5,708,183.

The invention relates to a novel process and to novel intermediates for preparing triazolinones which are in the main known and which can be used as intermediates for preparing herbicides and insecticides.

It is known that certain substituted triazolinones, such as the compound 4-methyl-5-trifluoromethyl-2,4-dihydro-3H-1,2,4-triazol-3-one, are obtained when corresponding triazolinethiones, such as the compound 4-methyl-5-trifluoromethyl-2,4-dihydro-3H-1,2,4-triazole-3-thione, are initially reacted with an alkylating agent, such as methyl iodide, in the presence of an acid binding agent, such as sodium methoxide, and the resulting alkylthiotriazole derivative is isolated in a customary manner, then heated with hydrogen peroxide in the presence of acetic acid, neutralized after cooling, and worked up in a customary manner (cf. U.S. Pat. No. 3,780,052—Example 2).

It is furthermore known that the abovementioned compound 4-methyl-5-trifluoro-methyl-2,4-dihydro-3H-1,2,4-triazol-3-one can also be obtained by heating 1-trifluoroacetyl-4-methyl-semicarbazide at 160° to 180° C., and subsequent extraction with ethyl acetate and column chromatography (cf. U.S. Pat. No. 3,780,052—Example 3).

However, the yield and quality of the resulting products are very unsatisfactory in both the cited synthesis methods.

Additional processes for preparing triazolinones are the subject of preceding but not prepublished applications (cf. DE-4 339 412 and DE-4 342 190).

The present application relates to a novel process for preparing triazolinones of the general formula (I)

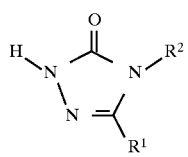

in which
R$^1$ represents halogenoalkyl, and
R$^2$ represents hydrogen, hydroxyl or amino, or represents alkyl, alkenyl, alkinyl, alkoxy, alkylamino, dialkylamino, cycloalkyl, cycloalkylalkyl, phenyl or phenylalkyl, characterized in that hydrazinecarboxylic esters of the general formula (II)

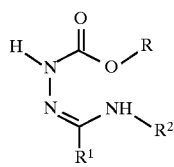

in which
R$^1$ and R$^2$ have the abovementioned meanings, and
R represents alkyl or aryl which are in each case optionally substituted,—and/or compounds which are tautomeric to the compounds of the formula (II)— are reacted in the presence of a basic reaction auxiliary and in the presence of a diluent, at temperatures of between 0° C. and 150° C.

Surprisingly, the triazolinones of the general formula (I) can be obtained in a simple manner and in very high yields by the novel process, with it being possible to vary the substituents over a wide range.

At the same time, safety problems, such as the use of hydrogen peroxide in previous processes, and effluent problems of a substantial nature, such as occur in connection with sulphur-containing effluents in previous processes, are avoided.

The novel process thus represents a valuable enrichment of the state of the art.

According to the novel process, compounds of the formula (I) are preferably prepared
in which
R$^1$ represents halogenoalkyl having from 1 to 6 carbon atoms, and
R$^2$ represents hydrogen, hydroxyl or amino, represents alkyl, alkenyl, alkinyl, alkoxy, alkylamino or dialkylamino which are in each case optionally substituted by cyano, halogen or C$_1$–C$_4$-alkoxy and which have in each case up to 6 carbon atoms in the alkyl, alkenyl or alkinyl groups, or represents C$_3$–C$_6$-cycloalkyl, C$_3$–C$_6$-cycloalkyl-C$_1$–C$_2$-alkyl, phenyl or phenyl-C$_1$–C$_2$-alkyl which are in each case optionally substituted by cyano, halogen, C$_1$–C$_4$-alkyl, C$_1$–C$_4$-alkoxy or C$_1$–C$_4$-alkoxycarbonyl.

The hydrocarbon radicals which are mentioned in the radical definitions, such as alkyl, are straight-chain or branched, even when this is not expressly indicated, as they also are in combinations with heteroatoms such as in alkoxy, alkylthio or alkylamino.

In general, halogen represents fluorine, chlorine, bromine or iodine, preferably represents fluorine, chlorine or bromine, and, in particular, represents fluorine or chlorine.

According to the novel process, compounds of the formula (I) are in particular prepared
in which
R$^1$ represents methyl, ethyl, n- or i-propyl, or n-, i- or s-butyl which are in each case substituted by fluorine and/or chlorine, and
R$^2$ represents methyl, ethyl, n- or i-propyl, n-, i- or s-butyl, allyl, propargyl, methoxy, ethoxy, n- or i-propoxy, n-, i- or s-butoxy, methylamino, ethylamino, n- or i-propylamino, n- or i- or s-butylamino, dimethylamino or diethylamino which are in each case optionally substituted by fluorine, chlorine, cyano, methoxy or ethoxy, or represents cyclopropyl, cyclobutyl, cyclopentyl, cyclohexyl, phenyl or benzyl which are in each case optionally substituted by fluorine, chlorine, bromine, cyano, methyl, ethyl, n- or i-propyl, methoxycarbonyl or ethoxycarbonyl.

A very particularly preferred group of compounds which can be prepared by the novel process are the compounds of the formula (I)
in which
R$^1$ represents methyl or ethyl which are in each case correspondingly substituted once, twice, three times, four times or five times by fluorine and/or chlorine, and
R$^2$ represents methyl, ethyl, n- or i-propyl, methoxy, ethoxy, methylamino, ethylamino, dimethylamino or cyclopropyl.

The above-listed general radical definitions, or the radical definitions given in preference ranges, apply both to the end products of the formula (I) and also, in a corresponding manner, to the starting compounds or intermediates which are in each case required for the preparation. These radical definitions can be combined at will among themselves, that is also between the given ranges of preferred compounds.

If, for example, ethyl 2-(2,2-difluoro-1-ethylimino-ethyl)hydrazine-1-carboxylate is used as the starting compound, the course of the reaction in the novel process can then be outlined by the following formula scheme:

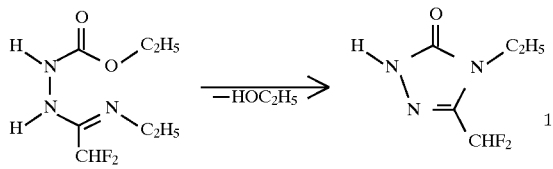

The hydrazinecarboxylic esters which are to be used as starting compounds in the novel process for preparing the compounds of the general formula (I) are defined generally by the formula (II). In the formula (II), $R^1$ and $R^2$ preferably or in particular have those meanings which have already been indicated above, in connection with the description of the compounds of the formula (I), as being preferred or in particular preferred for $R^1$ and $R^2$;

R preferably represents alkyl which is optionally substituted by halogen or $C_1$–$C_4$-alkoxy and which has 1 to 4 carbon atoms, or preferably represents phenyl which is optionally substituted by halogen or $C_1$–$C_4$-alkyl, and represents, in particular, methyl, ethyl, methoxyethyl, ethoxyethyl or phenyl.

The hydrazinecarboxylic esters of the formula (II) have not yet been disclosed in the literature; as novel compounds, they belong to the subject-matter of the present application.

The novel compounds of the general formula (II) are obtained when corresponding hydrazinecarboxylic esters of the general formula (III)

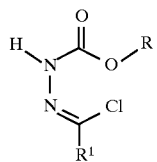 (III)

in which

R and $R^1$ have the abovementioned meanings, are reacted with amino compounds of the general formula (IV)

$H_2N$—$R^2$ (IV)

in which $R^2$ has the abovementioned meaning, where appropriate in the presence of an acid acceptor, such as triethylamine, and where appropriate in the presence of a diluent, such as acetonitrile or dioxane, at temperatures of between 0° C. and 100° C. (cf. the Preparation Examples).

The hydrazinecarboxylic esters used as precursors are defined generally by the formula (III). In the formula (III), $R^1$ and R preferably or in particular have those meanings which have already been indicated above, in connection with the description of the compounds of the formula (I) or of the formula (II), as being preferred or in particular preferred for $R^1$ and R.

The hydrazinecarboxylic esters of the formula (III) have not yet been disclosed in the literature; as novel compounds they belong to the subject-matter of the present application.

The novel compounds of the general formula (III) are obtained when corresponding hydrazinecarboxylic esters of the general formula (V)

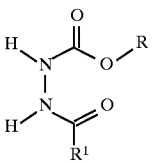 (V)

in which

R and $R^1$ have the abovementioned meanings, are reacted with a sulphonyl chloride, such as methane-, ethane-, benzene- or p-toluene-sulphonyl chloride, where appropriate in the presence of an acid acceptor, such as triethytamine or N,N-dimethyl-benzylamine, and where appropriate in the presence of a diluent, such as dimethoxyethane, dioxane, tetrahydrofuran, methylene chloride, ethyl acetate, toluene, chlorobenzene, acetone, methyl ethyl ketone, methyl isopropyl ketone, methyl isobutyl ketone, acetonitrile, propionitrile or butyronitrile, at temperatures of between 0° C. and 100° C. (cf. the Preparation Examples).

The hydrazinecarboxylic esters to be used as precursors in this context are defined generally by the formula (V). In the formula (V), $R^1$ and R preferably or in particular have those meanings which have already been indicated above, in connection with the description of the compounds of the formula (I) or of the formula (II), as being preferred or in particular preferred for $R^1$ and R.

The hydrazinecarboxylic esters of the formula (V) are known and/or can be prepared by known methods (cf. Synthesis 1991, 350–352; FR-2 123 205).

The hydrazinecarboxylic esters of the formula (Va)

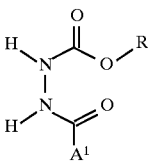 (Va)

in which $A^1$ represents dichloromethyl, trichloromethyl, difluoromethyl or trifluoromethyl, and R has the abovementioned meaning, have not yet been disclosed in the literature and, as novel compounds, belong to the subject-matter of the present application.

The novel hydrazinecarboxylic esters of the formula (Va) are obtained when hydrazinecarboxylic esters of the formula (VI)

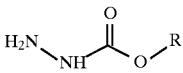 (VI)

in which

R has the abovementioned meaning, are reacted with carboxylic acids, or their derivatives, of the general formula (VII)

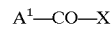 (VII)

in which $A^1$ has the abovementioned meaning, and

X represents hydroxyl, haloen (in particular fluorine or chlorine) or the group —O—CO—$A^1$, where appropriate in the presence of a diluent, such as diethyl ether, acetonitrile, propionitrile, butyronitrile, chlorobenzene, xylene or toluene, and at temperatures of between 0° C. and 150° C. (cf. the Preparation Examples).

The precursors of the formulae (VI) and (VII) are known synthesis chemicals.

The novel process is carried out in the presence of a basic reaction auxiliary. All the customary inorganic or organic bases are suitable for use as such an auxiliary. These bases include, for example, alkali metal or alkaline earth metal hydrides, hydroxides, amides, alcoholates, acetates, carbonates or hydrogen carbonates, such as lithium, sodium, potassium or calcium hydride, lithium, sodium, potassium or calcium hydroxide, lithium, sodium or potassium amide, sodium or potassium methoxide, sodium or potassium ethoxide, sodium or potassium propoxide, aluminium isopropoxide, sodium or potassium tert-butoxide, sodium or potassium hydroxide, ammonium hydroxide, sodium, potassium or calcium acetate, ammonium acetate, sodium, potassium or calcium carbonate, ammonium carbonate or sodium or potassium hydrogen carbonate, as well as basic organic nitrogen compounds, such as trimethylamine, triethylamine, tripropylamine, tributylamine, ethyl-diiso-propylamine, N,N-dimethylcyclohexylamine, dicyclohexylamine, ethyl-dicyclohex-ylamine, N,N-dimethylaniline, N,N-dimethylbenzylamine, pyridine, 2-methyl-, 3-methyl-and 4-methylpyridine, 2,4-dimethyl-, 2,6-dimethyl-, 3,4-dimethyl-and 3,5-dimethyl-pyridine, 5-ethyl-2-methyl-pyridine, N-methyl-piperidine, 4-dimethylamino-pyridine, diazabicyclooctane (DABCO), diazabicyclononene (DBN) or diazabicycloundecene (DBU).

Alkali metal hydroxides, such as sodium or potassium hydroxide, or alkali metal alcoholates, such as sodium methoxide, are particularly preferred as basic reaction auxiliaries in the novel process.

The amino compounds of the formula (IV)—see above—to be employed for preparing the starting compounds of the formula (II) can also be used as basic reaction auxiliaries in place of the abovementioned basic reaction auxiliaries.

The customary organic solvents are, in addition to water, suitable for use as diluents for carrying out the novel process. These solvents include, in particular, aliphatic, alicyclic or aromatic, optionally halogenated hydrocarbons, such as pentane, hexane, heptane, petroleum ether, ligroin, benzine, benzene, toluene, xylene, chlorobenzene, dichlorobenzene, cyclohexane, methylcyclohexane, dichloromethane, chloroform or tetrachloromethane; ethers, such as diethyl ether, diisopropyl ether, t-butyl methyl ether, t-pentyl methyl ether, dioxane, tetrahydrofuran, ethylene glycol dimethyl ether, ethylene glycol diethyl ether, diethylene glycol dimethyl ether or diethylene glycol diethyl ether; ketones, such as acetone, butanone or methyl isobutyl ketone; nitriles, such as acetonitrile, propionitrile, butyronitrile or benzonitrile; amides, such as N,N-dimethylformamide, N,N-dimethylacetamide, N-methylformanilide, N-methyl-pyrrolidone or hexamethylphosphoric triamide; esters, such as methyl, ethyl, n- or i-propyl or n-, i- or s-butyl acetate; sulphoxides, such as dimethyl sulphoxide; alcohols, such as methanol, ethanol, n- or i-propanol, n-, i-, s- or t-butanol, ethylene glycol monomethyl ether, ethylene glycol monoethyl ether, diethylene glycol monomethyl ether or diethylene glycol monoethyl ether; and also their mixtures with water, or pure water.

Water and methanol are particularly preferred for use as diluents in the novel process.

When carrying out the novel process, the reaction temperatures can be varied over a relatively wide range. In general, temperatures of between 0° C. and 150° C., preferably temperatures of between 10° C. and 120° C., in particular temperatures of between 20° C. and 110° C., are employed.

In general, the novel process is carried out under standard pressure. However, it is also possible to carry it out under elevated or reduced pressure—in general between 0.1 bar and 10 bar.

In order to carry out the novel process for preparing the compounds of the formula (I), from 1 to 3 mol, preferably from 1.5 to 2.5 mol, of basic reaction auxiliary are generally employed per mol of hydrazinecarboxylic ester of the formula (II).

In a preferred embodiment of the novel process, the hydrazinecarboxylic ester of the formula (II) is taken up in a suitable diluent at room temperature (approximately 20° C.) and, after a basic reaction auxiliary has been added, this mixture is stirred at an increased temperature until the reaction is complete. The mixture is then cooled down to room temperature (approximately 20° C.) once again and acidified with a strong acid, such as hydrochloric acid or sulphuric acid. If the product of the formula (I) crystallizes out under these circumstances, it can be isolated by filtering off with suction. Otherwise, the product of the formula (I) is extracted with an organic solvent, such as ethyl acetate, which is virtually immiscible with water, and the solvent is then distilled off from the organic phase, where appropriate after drying and filtering the latter, under reduced pressure, with the product of the formula (I) then remaining in the residue.

In a further, preferred embodiment of the novel process—in a "one-pot variant" as it were—the hydrazinecarboxylic esters of the formula (II), which are required as starting compounds, are prepared by reacting hydrazinecarboxylic esters of the formula (III) with amino compounds of the formula (IV), as described above, and are then converted without intermediate isolation—"in situ"—into the triazolinones of the formula (I).

For this purpose, a hydrazinecarboxylic ester of the formula (III) is preferably initially added, at a moderately increased temperature, preferably between 25° C. and 35° C., to a mixture consisting of an excess of an amino compound of the formula (IV)—in general between 2 and 10 mol, preferably between 2.5 and 5.0 mol—and a suitable diluent—preferably water. The reaction mixture is then heated at a temperature which is increased still further until the reaction is complete and then worked up as described above.

The triazolinones of the formula (I) which are to be prepared by the novel process can be used as intermediates for preparing active compounds which are of agricultural value (cf. U.S. Pat. No. 3,780,052, U.S. Pat. No. 3,780,053, U.S. Pat. No. 3 780 054 and EP-A-341489).

PREPARATION EXAMPLES

EXAMPLE 1

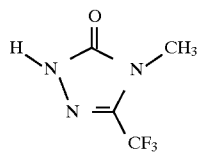

36 g (185 mmol) of methyl 2-(2,2,2-trifluoro-1-methylimino-ethyl)-hydrazine-1-carboxylate are suspended in 200 ml of water and, after 37.5 g of a 45% aqueous solution of sodium hydroxide (corresponding to 370 mmol of NaOH) have been added, the mixture is heated under reflux for 3 hours. After it has been cooled down to room temperature (approximately 20° C.), it is acidified with conc. hydrochloric acid and extracted three times with 100 ml of ethyl acetate on each occasion. The combined organic extraction solutions are dried with sodium sulphate and filtered. The solvent is carefully distilled off from the filtrate in a water suction vacuum.

28.9 g (93.5% of theory) of 4-methyl-5-trifluoromethyl-2,4-dihydro-3H-1,2,4-tria-zol-3-one are obtained as a solid residue.

$^1$H-NMR (DMSO-D$_6$, δ): 3.256 ppm (s, 3H), 12.655 ppm (s, 1H)

EXAMPLE 2

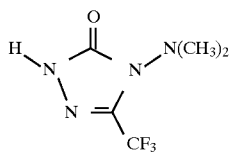

25.4 g (110 mmol) of methyl 2-(2,2,2-trifluoro-1-dimethylamino-ethylidene)-hydrazine-1-carboxylate are suspended in 200 ml of water and, after 19.8 g of a 45% aqueous solution of sodium hydroxide (corresponding to 223 mmol of NaOH) have been added, the mixture is heated under reflux for 3 hours. After it has been cooled down to room temperature (approximately 20° C.), it is acidified with conc. hydrochloric acid, and the product, which has crystallized out, is isolated by filtering it off with suction.

19.1 g (89% of theory) of 4-dimethylamino-5-trifluoromethyl-2,4-dihydro-3H-1,2,4-triazol-3-one are obtained with a melting point of 138° C.

EXAMPLE 3

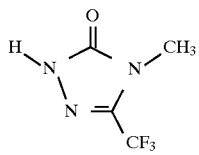

10.2 g (50 mmol) of methyl 2-(1-chloro-2,2,2-trifluoro-ethylidene)-hydrazine-1-carboxylate are added in portions to a mixture consisting of 50 ml of water and 22.5 g of a 34% aqueous solution of methylamine (corresponding to 250 mmol of methylamine), with the temperature of the mixture being maintained at between 25° C. and 35° C. The reaction mixture is subsequently heated under reflux for 2 hours and then, after having been cooled down to room temperature (approximately 20° C.), acidified with conc. hydrochloric acid. It is then extracted three times with ethyl acetate. The combined extraction solutions are dried with sodium sulphate and filtered. The solvent is then carefully distilled off from the filtrate in a water suction vacuum.

7.3 g (85% of theory) of 4-methyl-5-trifluoromethyl-2,4-dihydro-3H-1,2,4-triazol -3-one are obtained as a solid residue.

(Purity: 97.0%).

The compounds of the formula (I) listed in Table 1 below can also, for example, be prepared in analogy with Examples 1 to 3 and in accordance with the general description of the novel preparation process.

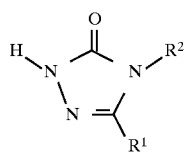

TABLE 1

Examples of the compounds of the formula (I) which are obtained in accordance with the invention

| Ex. No. | R$^1$ | R$^2$ | Yield (% of theory) | Physical Data |
|---|---|---|---|---|
| 4 | CF$_3$ | (CH$_2$)$_2$OCH$_3$ | 92 | n$_D^{20}$ = 1.4290 |
| 5 | CF$_3$ | (CH$_2$)$_3$OCH$_3$ | 90 | n$_D^{20}$ = 1.4320 |
| 6 | CHF$_2$ | CH$_3$ | | |
| 7 | CF$_2$Cl | CH$_3$ | | |
| 8 | CF$_3$ | H | 70 | m.p.: 198° C. |

STARTING COMPOUNDS OF THE FORMULA (II)

EXAMPLE (II-1)

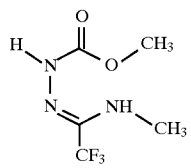

39.6 g (185 mmol) of methyl 2-(1-chloro-2,2,2-trifluoro-ethylidene)-hydrazine-1-carboxylate are dissolved in 220 ml of dioxane, and 50 g of a 34.5% aqueous solution of methylamine (corresponding to 556 mmol of methylamine) are added dropwise, at 20° C. to this solution within the space of 30 minutes, with the internal temperature being maintained at between 25° C. and 35° C. The mixture is then stirred at approximately 30° C. for a further 2 hours, after which it is concentrated in a water suction vacuum. The residue is stirred up with 150 ml of water and the product, which has crystallized out, is isolated by filtering it off with suction.

36 g (98% of theory) of methyl 2-(2,2,2-trifluoro-1-methyhimino-ethyl)-hydrazine-1-carboxylate are obtained.

$^1$H-NMR (DMSO-D$_6$, δ): 2.817 ppm (m, 3H), 3.641 ppm (s, 3H), 6.483 ppm (br. s, 1H), 9.527 ppm (s, 1H)

EXAMPLE (II-2)

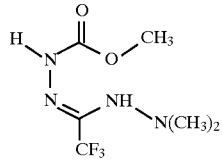

8.06 g (134 mmol) of N,N-dimethyl-hydrazine and 17 ml (122 mmol) of triethylamine are initially introduced in 120 ml of acetonitrile, and a solution of 25 g (122 mmol) of methyl 2-(1-chloro-2,2,2-trifluoro-ethylidene)-hydrazine-1-carboxylate in 30 ml of acetonitrile is added dropwise, at an internal temperature of approximately 55° C. and whilst stirring. The mixture is then stirred at 60° C. for a further hour, after which it is concentrated in a water suction vacuum. The residue is taken up in ethyl acetate and this solution is washed with water, dried with sodium sulphate and filtered. The filtrate is concentrated in a water suction vacuum and the residue is crystallized by digesting with diisopropyl ether, and the crystalline product is isolated by filtering it off with suction.

16.1 g (58% of theory) of methyl 2-(2,2,2-trifluoro-1-(N,N-dimethylhydrazino)-ethyl)-hydrazine-1-carboxylate are obtained with a melting point of 124° C.

The compounds of the formula (II) listed in Table 2 below can also, for example, be prepared in analogy with Examples (II-1) and (II-2).

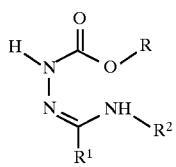
(II)

TABLE 2

Examples of the compounds of the formula (II)

| Ex. No. | $R^1$ | $R^2$ | R | Yield (% of theory) | Melting point (°C.) |
|---|---|---|---|---|---|
| II-3 | $CF_3$ | $CH_3$ | $CH_3$ | 88 | 213 |
| II-4 | $CF_3$ | $(CH_2)_2OCH_3$ | $CH_3$ | 68 | 150 |
| II-5 | $CF_3$ | $(CH_2)_3OCH_3$ | $CH_3$ | 84 | 148 |
| II-6 | $CF_3$ | OH | $CH_3$ | 63 | 183 |
| II-7 | $CF_3$ | $OCH_3$ | $CH_3$ | 27 | 104 |
| II-8 | $CHF_2$ | $CH_3$ | $CH_3$ | | |
| II-9 | $CF_2Cl$ | $CH_3$ | $CH_3$ | | |

PRECURSORS OF FORMULA (III)

EXAMPLE (III-1)

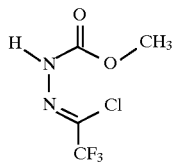

65.1 g (350 mmol) of methyl 2-trifluoroacetyl-hydrazine-1-carboxylate and 66.2 g (375 mmol) of benzenesulphonyl chloride are initially introduced in 450 ml of acetone, and a solution of 48.7 ml (350 mmol) of triethylamine in 50 ml of acetone is added dropwise, at an internal temperature of between 50° C. and 55° C. and while stirring. After the reaction mixture has been stirred at from 50° C. to 55° C. for 1 hour, 2.5 ml of triethylamine are added to it and the stirring is continued for a further 30 minutes. After the mixture has been cooled in an ice bath, the triethylammonium chloride, which has crystallized out, is separated off by filtering with suction. The filtrate is concentrated in a water suction vacuum and the residue is taken up in 300 ml of ethyl acetate; this solution is washed three times with 100 ml of water on each occasion, dried with sodium sulphate and filtered. The solvent is carefully distilled off from the filtrate in a water suction vacuum.

72.5 g (purity: 92.2%, yield: 93% of theory) of methyl 2-(1-chloro-2,2,2-trifluoroethylidene)-hydrazine-1-carboxylate are obtained as a solid product.

$^1$H-NMR (DMSO-$D_6$, δ): 3.78 ppm (s, 3H), 11.59 ppm (s, 1H) The compounds of the formula (III) listed in Table 3 below can also, for example, be prepared in analogy with Example (III-1).

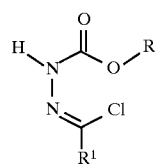
(III)

TABLE 3

Examples of the compounds of the formula (III)

| Ex. No. | R1 | R | Yield (% of theory) | Melting Point (°C.) |
|---|---|---|---|---|
| III-2 | $CHF_2$ | $CH_3$ | | |
| III-3 | $CF_2Cl$ | $CH_3$ | | |

PRECURSORS OF THE FORMULA (V)

EXAMPLE (V-1)

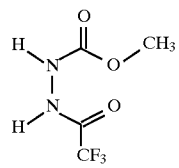

121.5 g (1.28 mol) of methyl carbazate (methyl hydrazinecarboxylate) are initially introduced in 1200 ml of diethyl ether, and 310 g (1.48 mol) of trifluoroacetic anhydride are added dropwise, at 0° C, within the space of 2 hours. The mixture is then stirred at from 0° C. to 20° C. for about a further 90 minutes, after which it is concentrated in a water suction vacuum; the residue is stirred up with 500 ml of toluene, and the crystalline product is isolated by filtering it off with suction.

219 g (purity: 94.4%, yield: 94% of theory) of methyl 2-trifluoroacetylhydrazine-1-carboxylate are obtained with a melting point of 105° C.

$^1$H-NMR (DMSO-$D_6$, δ): 3.647 ppm (s, 3H), 9.649 ppm (s, IH), 11.429 ppm (s, IH).

EXAMPLE (V-2)

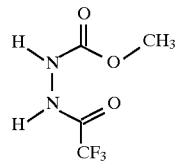

18.5 g (0.20 mol) of methyl carbazate (methyl hydrazinecarboxylate) are initially introduced in 150 ml of toluene, and 23.1 ml (0.30 mol) of trifluoroacetic acid are added dropwise, at an internal temperature of 80° C., within the space of 35 minutes. The mixture is then stirred at 80° C. for a further 30 minutes, after which it is heated for one hour on a water separator and then concentrated in a water suction vacuum. The residue is stirred up with 500 ml of toluene, and the crystalline product is isolated by filtering it off with suction.

36.4 g (purity: 90.1%, yield: 88.2% of theory) of methyl 2-trifluoroacetyl-hydrazine-1-carboxylate are obtained with a melting point of 105° C.

It will be understood-that the specification and examples are illustrative but not limitative of the present invention and that other embodiments within the spirit and scope of the invention will suggest themselves to those skilled in the art.

I claim:

1. A Hydrazinecarboxylic ester of the general formula (II)

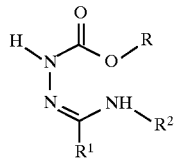 (II)

wherein

R represents $C_{1-4}$-alkyl, which is optionally substituted by halogen or $C_{1-4}$-alkoxy, or represents phenyl, which is optionally substituted by halogen or $C_{1-4}$-alkyl, $R^1$ represents halogenoalkyl, and $R^2$ represents $C_{1-6}$-alkyl, $C_{1-4}$-alkoxy-$C_{1-6}$-alkyl, amino, $C_{1-6}$-alkylamino, or di-$C_{1-6}$-alkylamino.

2. A process for preparing hydrazinecarboxylic esters of the general formula (II)

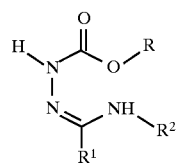 (II)

wherein

R, $R^1$ and $R^2$ have the meanings given in claim 1, by reacting corresponding hydrazinecarboxylic esters of the general formula (III)

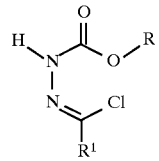 (III)

wherein

R and $R^1$ have the abovementioned meanings, with amino compounds of the general formula (IV)

 (IV)

wherein $R^2$ has the abovementioned meaning, optionally in the presence of an acid acceptor and optionally in the presence of a diluent, at temperataures of between 0° C. and 100° C.

* * * * *